United States Patent
Consiglio et al.

(10) Patent No.: US 11,517,669 B2
(45) Date of Patent: Dec. 6, 2022

(54) PIEZOELECTRIC MEMBRANE PUMP FOR THE INFUSION OF LIQUIDS

(71) Applicant: KONINKLIJKE PHILIPS N.V., Eindhoven (NL)

(72) Inventors: Ronald Paul Consiglio, Clermont, FL (US); Francis Patrick O'Neill, Kissimmee, FL (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 91 days.

(21) Appl. No.: 16/333,271

(22) PCT Filed: Sep. 29, 2017

(86) PCT No.: PCT/EP2017/074915
§ 371 (c)(1),
(2) Date: Mar. 14, 2019

(87) PCT Pub. No.: WO2018/060505
PCT Pub. Date: Apr. 5, 2018

(65) Prior Publication Data
US 2019/0247577 A1    Aug. 15, 2019

Related U.S. Application Data

(60) Provisional application No. 62/401,244, filed on Sep. 29, 2016.

(51) Int. Cl.
*A61M 5/168* (2006.01)
*A61M 5/36* (2006.01)
(Continued)

(52) U.S. Cl.
CPC ........ *A61M 5/16831* (2013.01); *A61M 5/145* (2013.01); *A61M 5/14224* (2013.01);
(Continued)

(58) Field of Classification Search
CPC .............. A61M 5/007; A61M 5/14224; A61M 5/145; A61M 5/16831; A61M 5/16854;
(Continued)

(56) References Cited

U.S. PATENT DOCUMENTS

| 5,630,709 A * | 5/1997 | Bar-Cohen ............ F04B 7/0076 417/322 |
| 5,759,014 A | 6/1998 | Van Lintel |
| 6,102,678 A * | 8/2000 | Peclat ................... A61M 5/142 417/474 |
| 6,555,986 B2 | 4/2003 | Moberg |
| 9,437,802 B2 | 9/2016 | Li |
| 2004/0085215 A1* | 5/2004 | Moberg ............ A61M 5/16854 340/679 |

(Continued)

FOREIGN PATENT DOCUMENTS

| EP | 0398583 | 11/1990 |
| EP | 0398583 A2 * | 11/1990 ............ F04B 7/0076 |

(Continued)

*Primary Examiner* — Kami A Bosworth

(57) ABSTRACT

An infusion pump including a fluid chamber having an outlet valve and a piezo-stack actuator including a stack of piezo-electric layers. The infusion pump also includes a linear actuator to measure displacement of the piezo-stack actuator during operation. An electronic processor is programmed to operate the outlet valve and the piezo-stack actuator to pump fluid through the fluid chamber at a programmed flow rate.

6 Claims, 3 Drawing Sheets

(51) Int. Cl.
*A61M 5/142* (2006.01)
*A61M 5/145* (2006.01)
*A61M 5/00* (2006.01)

(52) U.S. Cl.
CPC .............. *A61M 5/365* (2013.01); *A61M 5/007* (2013.01); *A61M 5/16854* (2013.01); *A61M 2005/14208* (2013.01); *A61M 2005/14506* (2013.01); *A61M 2005/16863* (2013.01); *A61M 2205/0244* (2013.01); *A61M 2205/0294* (2013.01); *A61M 2205/14* (2013.01); *A61M 2205/18* (2013.01); *A61M 2205/332* (2013.01); *A61M 2205/3334* (2013.01); *A61M 2205/3337* (2013.01); *A61M 2205/50* (2013.01); *A61M 2205/505* (2013.01)

(58) Field of Classification Search
CPC ........ A61M 5/365; A61M 2005/14208; A61M 2005/14506; A61M 2005/16863; A61M 2205/0244; A61M 2205/0294; A61M 2205/14; A61M 2205/18; A61M 2205/332; A61M 2205/3334; A61M 2205/3337; A61M 2205/50; F04B 17/003
See application file for complete search history.

(56) References Cited

U.S. PATENT DOCUMENTS

| | | | |
|---|---|---|---|
| 2006/0206054 A1* | 9/2006 | Shekalim | A61M 5/141 604/122 |
| 2009/0148317 A1* | 6/2009 | Pietron | F04B 43/046 417/413.2 |
| 2009/0214358 A1 | 8/2009 | O'Neill | |
| 2009/0311116 A1* | 12/2009 | Bai | F04B 43/04 417/413.2 |
| 2011/0034872 A1* | 2/2011 | Chiravuri | A61M 5/14276 604/132 |
| 2011/0251481 A1* | 10/2011 | Strobl | A61M 5/14546 600/420 |
| 2015/0314068 A1 | 11/2015 | Alderete | |
| 2019/0134297 A1* | 5/2019 | Kamen | A61M 5/142 |

FOREIGN PATENT DOCUMENTS

| | | |
|---|---|---|
| EP | 1403519 | 3/2004 |
| JP | 3001876 A | 1/1991 |
| JP | 2004024476 A | 1/2004 |
| JP | 2012506279 A | 3/2012 |
| WO | 200735563 | 3/2007 |
| WO | 2010/046728 | 4/2010 |
| WO | 2015/102078 | 7/2015 |

* cited by examiner

PIEZOELECTRIC MEMBRANE PUMP FOR THE INFUSION OF LIQUIDS

CROSS REFERENCE TO RELATED APPLICATIONS

This application is the U.S. National Phase application under 35 U.S.C. § 371 of International Application No. PCT/EP2017/074915 filed Sep. 29, 2017, published as WO 2018/060505 on Apr. 5, 2018, which claims the benefit of U.S. Provisional Patent Application No. 62/401,244 filed Sep. 29, 2016. These applications are hereby incorporated by reference herein.

FIELD

The following relates generally to the medical infusion arts, infusion pump arts, and related arts.

BACKGROUND

Volumetric infusion pumps deliver fluid to a patient intravascularly at a controlled flow rate. Depending upon the type of therapeutic fluid being delivered, interruption of the flow can present a serious patient safety issue. Such flow interruption can result from an occlusion in the fluid tubing, or from a disconnect of the fluid tubing at any point between the infusion pump and the patient. Similarly, the presence of bubbles in the infused fluid presents a safety concern.

Currently, infusion pumps for general use both in hospital and home incorporate free flow prevention, occlusion detection, and bubble detection as separate systems. Typically there is no indication of disconnection from the patient or downstream leakage.

In addition, current infusion pumps for use in MR environments use ultrasonic Piezo elements, and are complex, expensive, inaccurate, unreliable and have high power consumption.

Improvements disclosed herein address the foregoing and other disadvantages of existing infusion pump systems, methods, and the like.

BRIEF SUMMARY

In accordance with one illustrative example, an infusion pump includes a fluid chamber having an outlet valve, and a piezo-stack actuator comprising a stack of piezo-electric layers. An electronic processor is programmed to operate the outlet valve and the piezo-stack actuator to pump fluid through the fluid chamber at a programmed flow rate.

In accordance with another illustrative example, a method of using an infusion pump with a fluid chamber that is pumped by a pump motor comprising a piezo-stack actuator is provided. The method includes: with a linear encoder, measuring a displacement of the piezo-stack actuator during operation of the piezo-stack actuator; with at least one processor, comparing the measured displacement to a reference value to detect the presence of at least one of bubbles in a fluid chamber of the motor, the presence of occlusions in a tube connected to an outlet valve of the fluid chamber, or the presence of line disconnections of the tube connected to the outlet valve of the fluid chamber; and with the at least one processor, outputting a warning indicating the presence of at least one of the bubbles, occlusions and tube disconnections.

In accordance with another illustrative example, an infusion pump includes a fluid chamber having an outlet valve, and a piezo-stack actuator comprising a stack of piezoelectric layers. A linear encoder is connected to the fluid chamber. The linear encoder is configured to measure a displacement of the piezo-stack actuator during operation of the piezo-stack actuator. An electronic processor is programmed to: operate the outlet valve and the piezo-stack actuator to pump fluid through the fluid chamber at a programmed flow rate; and read the linear encoder and, based on the displacement of the piezo-stack actuator measured by the linear encoder, detect the presence of each of: bubbles in the fluid chamber, a tube occlusion, or a tube disconnection.

One advantage resides in providing an infusion pump with a piezo-stack actuator.

Another advantage resides in providing an infusion pump with a piezo-stack actuator and an integrated sensor that detects the presence of bubbles, occlusions, and tube disconnections.

Further advantages of the present disclosure will be appreciated to those of ordinary skill in the art upon reading and understand the following detailed description. It will be appreciated that a given embodiment may provide none, one, two, or more of these advantages.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the invention.

DETAILED DESCRIPTION

Figure 1:
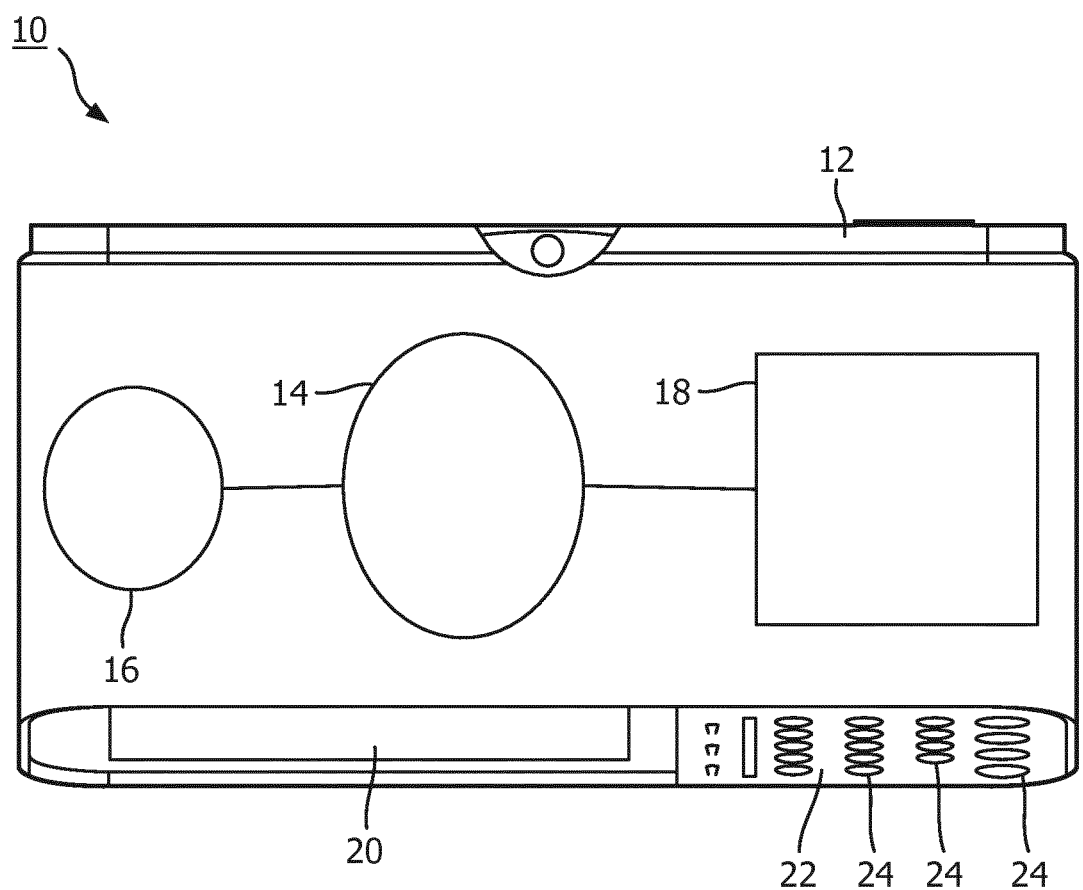
FIG. 1 diagrammatically illustrates a top view of medical device in accordance with one aspect.

The following relates to volumetric infusion pumps, which have application by way of illustration as MR-compatible infusion pumps. The disclosed volumetric infusion pumps employ fluid chamber pumped by a linear motor in the form of a piezo-stack actuator, consisting of a stack of piezoelectric elements that expands under electrical bias. The choice has a number of advantages over conventional rotary piezoelectric motors, such as less susceptibility to wear and potentially lower cost.

Another advantage of the chosen piezo-stack actuator is that it can be used to detect bubbles, tube occlusions, or tube disconnects. This entails adding a linear encoder to measure the linear displacement of the piezo-stack actuator.

To detect bubbles, the outlet valve of the pump chamber is closed while the piezo-stack actuator is running. As water-based medicines are essentially incompressible while air is highly compressible, the compressibility of the trapped fluid in the pump chamber is a measure of the absence or presence of air bubbles. Specifically, air bubbles will increase compressibility. The compressibility is measured using the linear encoder to measure the linear displacement of the piezo-stack actuator under a reference electrical bias (which may optionally be the same as the operational electrical bias).

To detect tube occlusions or tube disconnects (more generally, tube resistance), a similar process is employed but with the outlet valve open. A tube occlusion will be picked up as decreased actuator movement under a reference electrical bias, while a tube disconnect will be detected as increased actuator movement under the reference electrical bias.

Since bubble detection employs a well-defined closed system, it may be reasonable to empirically calibrate the quantitative increase in linear displacement corresponding to an air bubble. On the other hand, tube resistance depends on numerous factors (e.g. tube length, tube path). To account for this, the calibration may be performed for various tube resistances, tube lengths, and/or tube paths of the tube connected to the outlet valve of the fluid chamber to develop a calibration parameterized by tube resistance, length, and/or path.

The following makes drug delivery in the MR safer and potentially more accurate by implementing a novel actuator that will allow greater delivery accuracy and the combination of several functions into a single component. The disclosed infusion pump motor comprising a piezo-stack actuator is simpler, has no pull and creates no audible noise as it operates at low frequency (i.e. below the audible range). The piezo-stack actuator consumes low power and allows for elimination of complex drive mechanisms. The control pulse shape may be managed to achieve proportional control.

A piezo-stack actuator, with or without mechanical advantage is used to drive a pump membrane. The work function of this stack actuator is known in one of 3 possible ways: (1) from the batch in which it was built if this is sufficiently controlled; (2) from characterization during build; and (3) from a self test function.

In some embodiments, the piezo-stack actuator serves as the motor of the infusion pump has a linear encoder attached directly linked to the point at which it drives the pump membrane. The relationship of the applied current/applied waveform and the resultant displacement of the pump head is known, e.g. by empirical calibration.

Bubble detection, occlusion detection and/or tube disconnection detection may be achieved through monitoring of the linear encoder response once the work function and input signal is known.

With reference now to FIG. 1, a schematic illustration of an infusion pump 10 is shown. The infusion pump 10 includes a housing 12 that encloses a fluid pump 14, a power source (or power converter, e.g. to convert 110V or 220V a.c. power to operating power) 16, and at least one electronic processor 18. FIG. 1 shows a top view of the infusion pump 10 with a "top" portion of the housing 12 is removed, so that the internal components disposed therein are visible. The fluid pump 14 is configured to operate the medical device 10 to deliver medication to a patient. The fluid pump 14 is powered by the power source 16 (e.g., a battery). The at least one processor 18 is programmed to control operations of the infusion pump 10, as described in more detail below.

The infusion pump 10 also includes a display 20 configured to display details of operations of the medical device 10, as described in more detail below. A keypad 22 (or dials, buttons, or other user controls) is disposed adjacent the display 20. The illustrative keypad 22 includes a plurality of keys 24.

The infusion pump 10 is of the volumetric infusion pump type, in which an intravascular (IV) fluid bag (not shown) is connected to an inlet of the infusion pump 10 and the fluid pump 14 draws fluid from the IV fluid bag and pumps it to an IV fluid line connecting with the patient at a controlled flow rate.

Figure 2:
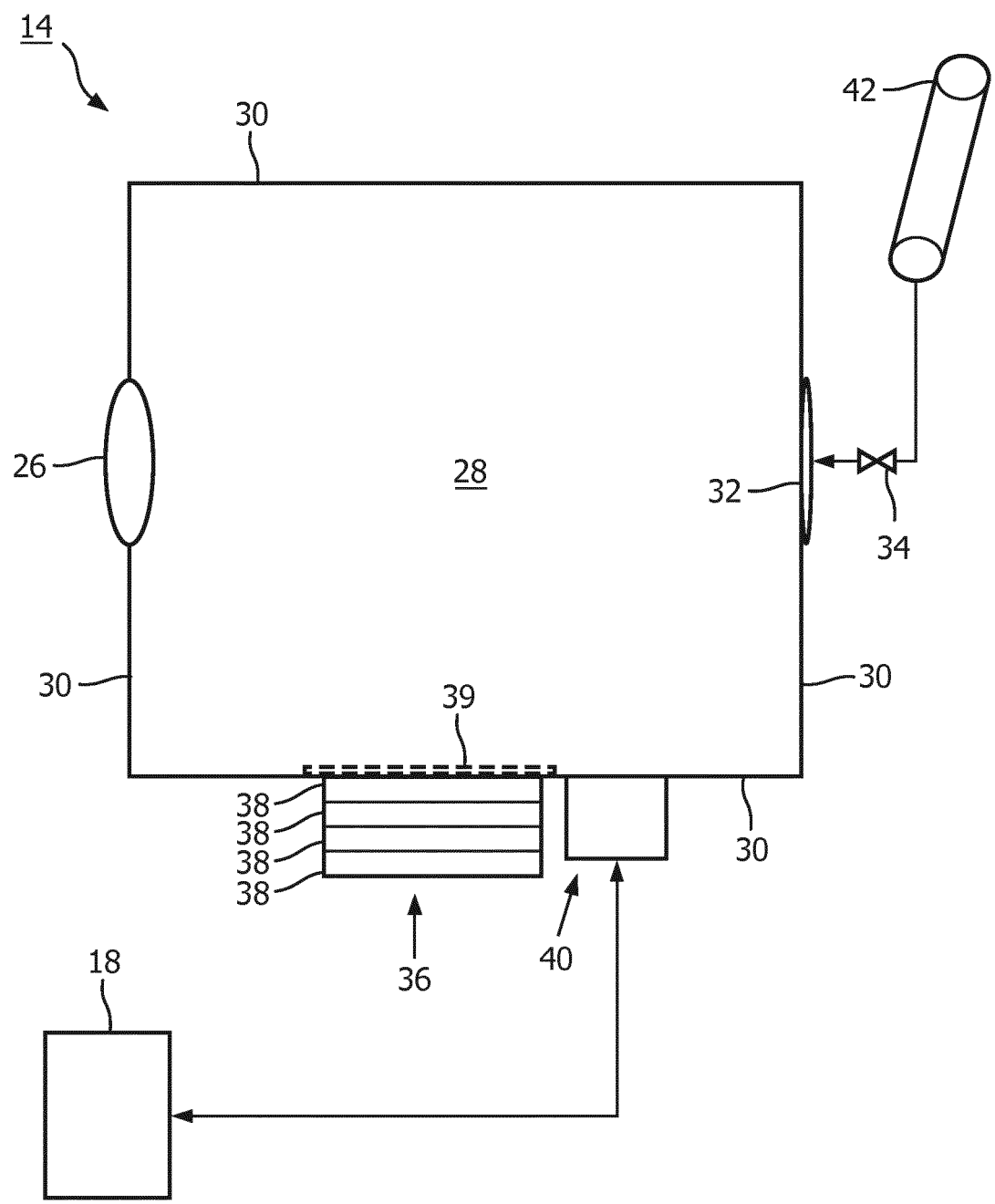
FIG. 2 diagrammatically illustrates a first operative state of the medical device of FIG. 1.
Figure 3:
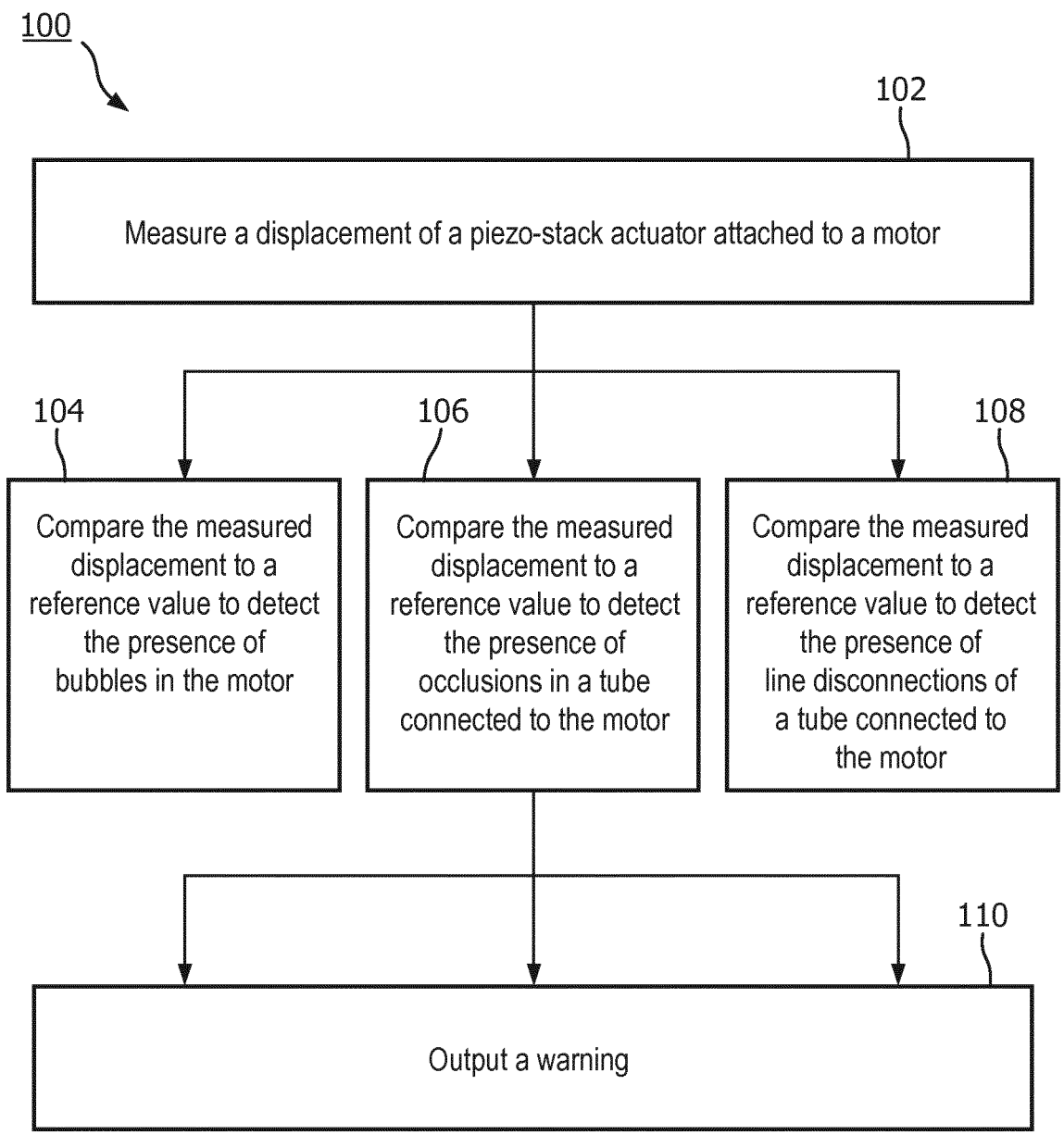
FIG. 3 diagrammatically illustrates a medical device illumination method suitably performed using the medical device of FIG. 1.

With reference now to FIG. 2, and with continuing reference to FIG. 1, the fluid pump 14 of the volumetric infusion pump 10 is shown in more detail. The fluid pump 14 includes an inlet 26 (optionally valved by an inlet valve, not shown) to a fluid chamber 28 defined by a plurality of walls 30. The fluid chamber 28 also has an outlet 32 valved by an outlet valve 34. As shown in FIG. 2, the inlet 26 and the outlet 32 are disposed on opposing walls 30 of the fluid chamber 28; however, in some examples, the inlet and the outlet are disposed on adjacent walls 30, or the same wall, of the fluid chamber 28. It is also noted that the outlet valve 34 may be variously placed, e.g. embedded into the wall of the fluid chamber 28 or connected to a tube extending out from the wall, or so forth.

The illustrative fluid pump 14 includes a piezo-stack actuator 36 comprising a stack of piezo-electric layers 38 which is connected to pump the fluid chamber 28. In the illustrative embodiment, the piezo-stack actuator 36 pushes against a pump membrane 39 formed into a proximate wall of the fluid chamber 28. The piezo-stack actuator 36 lengthens linearly in response to an applied electrical bias (e.g. voltage) in accordance with a piezo-electric property of the piezo-electric layers 38. This action deforms the pump membrane 39 inward so as to reduce the volume contained in the fluid chamber 28, thereby increasing pressure of the infusion fluid in the fluid chamber 28. Conversely, when the bias is removed (or reduced) the piezo-stack actuator 36 reduces in length, thereby increasing the volume and reducing the chamber pressure. In a typical operating sequence, the outlet valve 34 is closed, the electrical bias is applied to the fluid chamber 28 to pressurize it, the outlet valve 34 is opened to release fluid flow, then closed to complete the cycle. Some illustrative embodiments of the piezo-stack actuator 36 include can include a commercially-available actuator (e.g., from Viking AT, LLC, Sarasota, Fla.).

In embodiments employing integral sensing of bubbles, occlusions, and/or tube disconnects, a linear encoder 40 is connected to the piezo-stack actuator 36. The linear encoder 40 is configured to measure a displacement of the piezo-stack actuator 36 during operation of the piezo-stack actuator 36. As shown in FIG. 2, the linear encoder 40 is disposed adjacent the piezo-stack actuator 36; however, in some examples, the linear encoder 40 can be disposed on a different wall 30 than the wall that the piezo-stack actuator 36 is disposed on, or the linear encoder 40 can integrally formed with the piezo-stack actuator 36. The linear encoder 40 can be configured as any suitable sensor configured to measure a displacement of the piezo-stack actuator 36 during operation of the motor 14. For example, the linear encoder 40 may be an optical linear encoder, capacitive or inductive linear encoder, or so forth. A magnetic linear encoder is also contemplated, but is not preferred in the case of an MR-compatible infusion pump.

To provide bubble, occlusion, and/or disconnect detection, the at least one electronic processor 18 is programmed to read the linear encoder 40 and, based on the displacement of the piezo-stack actuator 36 measured by the linear encoder, detect the presence of at least one of bubbles in the fluid chamber 28, a tube occlusion, or a tube disconnection. In this context, a tube occlusion refers to a blockage of flow through a fluid tube 42 through which IV fluid is flowed into the patient's vascular system. The fluid tube 42 is connected at one end to the outlet 32 of the fluid pump 14 with the outlet valve 34 connected to control (e.g. valve on or off) flow of IV fluid from the fluid chamber 28 into the fluid tube 42. The opposite end of the fluid tube 42 is operatively connected to flow fluid into the patient's vascular system, e.g. connected with an IV cannula that is inserted into a vein (for intravenous infusion) or artery (for arterial infusion). A "tube occlusion" in this context refers to any blockage that prevents the fluid pump 14 from "seeing" the expected flow resistance at the outlet 32. Thus, it will be appreciated that an occlusion will be detected if the blockage is in the fluid tube 42, but will also be detected if the blockage is at the outlet 32 or in the cannula or other tube/patient coupling. Likewise, a "tube disconnect" as used herein refers to any disconnect that produces a low flow resistance as "seen" from the outlet 32. Thus, it will be appreciated that a tube disconnect will be detected if it occurs at the connection of the tube 42 with the outlet 32 of the fluid chamber 28, or if it occurs at the tube/cannula connection or of the cannula dislodges from the patient. In other embodiments, the electronic processor 18 is programmed to measure the displacement of the piezo-stack actuator 36 during operation of the piezo-stack actuator 36 to detect each of: the presence of bubbles in the fluid chamber 28, the presence of occlusions in the tube 42 connected to the outlet valve 34 of the fluid chamber, and the presence of line disconnections of the tube 42 connected to the outlet 32 of the fluid chamber 28.

In one example, as shown in FIG. 2, the at least one processor 18 is programmed to detect the presence of bubbles in the fluid chamber 28 based on the displacement of the piezo-stack actuator 36 during operation of the motor 14. To do so, the at least one processor 18 is programmed to read the linear encoder 40 during operation of the piezo-stack actuator 36 (i.e., while the fluid pump 14 is running) at a reference electrical bias and with the outlet valve 34 closed. A displacement value of the piezo-stack actuator 36 is measured by the linear encoder 40 at the reference electrical bias and with the outlet valve closed. From the measured displacement value, the at least one processor 18 is programmed to compare the measured displacement value with a bubbles detection threshold value that is programmed into the at least one processor. If the measured displacement is greater than the bubbles detection threshold value, then at least one bubble is present in the fluid chamber 28. Conversely, if the measured displacement is less than the bubbles detection threshold value, then there are no bubbles present in the fluid chamber 28. The at least one processor 18 is then programmed to output a warning (i.e., on a display, a warning sensor, an audible tone, and the like) to alert a user of the presence of bubbles.

In another example, the electronic processor 18 is programmed to detect the presence of occlusions in the tube 42 connected to the outlet valve 34 of the fluid chamber 28. To do so, the at least one processor 18 is programmed to read the linear encoder 40 during operation of the piezo-stack actuator 36 (i.e., while the motor 14 is running) at a reference electrical bias and with the outlet valve 32 open (as opposed to the bubble detection operation in which the outlet valve 34 is closed). A displacement value of the piezo-stack actuator 36 is measured by the linear encoder 40 at the reference electrical bias and with the outlet valve open. From the measured displacement value, the at least one processor 18 is programmed to compare the measured displacement value with an occlusion threshold value that is programmed into the at least one processor. The occlusion threshold value is a function of at least one of tube resistance, tube length, and tube path of the tube 42. If the measured displacement is less than the occlusion threshold value, then at least one occlusion is present in the tube 42. The at least one processor 18 is then programmed to output a warning (i.e., on a display, a warning sensor, an audible tone, and the like) to alert a user of the presence of occlusions.

In a further example, the electronic processor 18 is programmed to detect the presence of a tube disconnection (i.e., a disconnection between the tube 42 and the inlet value 32/outlet valve 34). To do so, the at least one processor 18 is programmed to read the linear encoder 40 during operation of the piezo-stack actuator 36 (i.e., while the motor 14 is running) at a reference electrical bias and with the outlet valve 32 open (similar to the occlusion detection operation). A displacement value of the piezo-stack actuator 36 is measured by the linear encoder 40 at the reference electrical bias and with the outlet valve open. From the measured displacement value, the at least one processor 18 is programmed to compare the measured displacement value with a disconnect threshold value that is programmed into the at least one processor. The disconnect threshold value is a function of at least one of tube resistance, tube length, and tube path of the tube 42. If the measured displacement is greater than the disconnect threshold value, then a tube disconnection is detected (i.e., between the tube 42 and the inlet value 32/outlet valve 34). The at least one processor 18 is then programmed to output a warning (i.e., on a display, a warning sensor, an audible tone, and the like) to alert a user of the presence of tube disconnections.

It will be appreciated that the medical device 10 (i.e., the infusion pump 10) is configured for use in an MR environment to avoid generating MR interference. To prevent generating MR interference, the components of the infusion pump 10, in particular the motor 14, are made from non-magnetic materials.

With reference now to FIG. 4, a method 100 of using a infusion pump 10 in an MR environment is shown. At step 102, a displacement of a piezo-stack actuator 36 attached to a motor 14 during operation of the motor is measured using a linear enconder 40. At optional step 104, with at least one processor 18, the measured displacement of the piezo-stack actuator 36 is compared to a reference value to detect the presence of bubbles in a fluid chamber 28 of the motor 14. At optional step 106, with the at least one processor 18, the measured displacement of the piezo-stack actuator 36 is compared to a reference value to detect the presence of occlusions in a tube 42 connected to the outlet 34 of the fluid chamber 28. At optional step 108, with at least one processor 18, the measured displacement of the piezo-stack actuator 36 is compared to a reference value to detect the presence of line disconnections of the tube 42 connected to the outlet valve 34 of the fluid chamber 28. At step 110, with at least one processor 18, a warning is outputted to a user to indicate the presence of at least one of the bubbles, occlusions and tube disconnections.

It will be appreciated that the illustrative data processing or data interfacing components of the medical device 10 may be embodied as a non-transitory storage medium storing instructions executable by an electronic processor (e.g. the at least one electronic processor 18) to perform the disclosed operations. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth.

The disclosure has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An infusion pump, comprising:
a fluid chamber having an outlet valve;
a pump membrane formed into a wall of the fluid chamber;
a piezo-stack actuator directly secured to the pump membrane formed into the wall of the fluid chamber, the piezo-stack actuator comprising a stack of piezo-electric layers that lengthens in response to an applied electrical bias to deform the pump membrane inward in the direction of the fluid chamber to reduce a volume of the fluid chamber thereby increasing a pressure of an infusion fluid within the fluid chamber;
a linear encoder connected to the fluid chamber, the linear encoder being configured to measure a displacement of the piezo-stack actuator during operation of the piezo-stack actuator; and
an electronic processor programmed to operate the outlet valve and the piezo-stack actuator to pump the infusion fluid through the fluid chamber at a programmed flow rate, wherein the electronic processor is further programmed to read the linear encoder and, based on the displacement of the piezo-stack actuator measured by the linear encoder, detect a tube occlusion of a tube operably connected to the outlet valve or a tube disconnection of the tube operably connected to the outlet valve, wherein the detection is further based on at least one of tube resistance, tube length, and tube path of the tube.

2. The infusion pump according to claim 1, wherein the electronic processor is programmed to measure the displacement of the piezo-stack actuator during operation of the piezo-stack actuator to detect each of: a presence of bubbles in the fluid chamber, occlusions in the tube connected to the outlet valve of the fluid chamber, and line disconnections of the tube connected to the outlet valve of the fluid chamber.

3. The infusion pump according to claim 1 wherein the electronic processor is programmed to detect a presence of bubbles in the fluid chamber by performing operations including:
reading the linear encoder during operation of the piezo-stack actuator at a reference electrical bias and with the outlet valve closed; and
detecting bubbles in the fluid chamber based on the measured displacement at the reference electrical bias and with the outlet valve closed being greater than a bubbles detection threshold value.

4. The infusion pump according to claim 1, wherein the electronic processor is programmed to detect the tube disconnection by performing operations including:
reading the linear encoder during operation of the piezo-stack actuator at a reference electrical bias and with the outlet valve open; and
detecting the tube disconnection based on the measured displacement at the reference electrical bias and with the outlet valve open being greater than a disconnect threshold value.

5. The infusion pump according to claim 4, wherein the disconnect threshold value is a function of the at least one of tube resistance, tube length, and tube path of the tube.

6. The infusion pump according to claim 1, wherein the infusion pump includes no magnetic material.

* * * * *